United States Patent [19]
Weber-Unger

[11] Patent Number: 5,690,122
[45] Date of Patent: Nov. 25, 1997

[54] ABDOMINAL BELT

[75] Inventor: Georg Weber-Unger, Kufstein, Austria

[73] Assignee: Anita International Dr. Helbig GmbH & Co. KG, Brannenburg, Germany

[21] Appl. No.: 732,144

[22] Filed: Oct. 16, 1996

[30] Foreign Application Priority Data

Oct. 19, 1995 [DE] Germany ............... 195 40 234.0

[51] Int. Cl.[6] ....................................................... A61F 5/37
[52] U.S. Cl. ..................................... 128/876; 602/19
[58] Field of Search ........................ 128/869, 873, 128/874, 875, 876, 96.1, 98.1, 100.1, 101.1, 106.1, 108.1; 602/19

[56] References Cited

U.S. PATENT DOCUMENTS 1,577,666  3/1926  Walter ............................. 128/96.1
3,116,736  1/1964  Alberts ............................ 128/98.1
3,273,563  9/1966  Bonang ........................... 128/96.1
5,060,639  10/1991 Marcus ............................ 602/19

FOREIGN PATENT DOCUMENTS 8708327  10/1987  Germany.

Primary Examiner—Michael A. Brown
Attorney, Agent, or Firm—Mark P. Stone

[57] ABSTRACT

In the case of an abdominal belt which can be closed by a touch-and-close fastener (6), use is made, for the purpose of large-surface-area support of the lower abdomen, of two supporting straps (1,2) which are connected to one another in the front belt region via a fabric bridge (5) made of highly elastic material. The supporting straps are cut and arranged such that they can be pushed one over the other in an imbricated manner when the individual wearing them sits down.

7 Claims, 1 Drawing Sheet

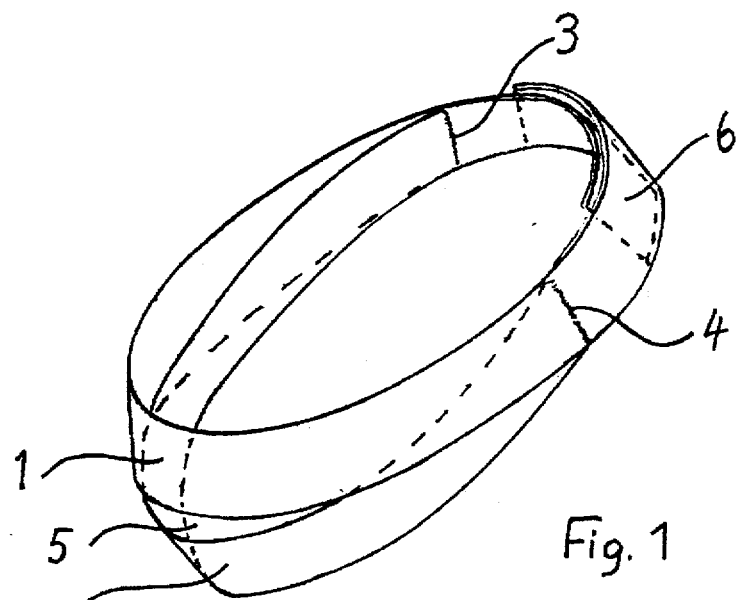
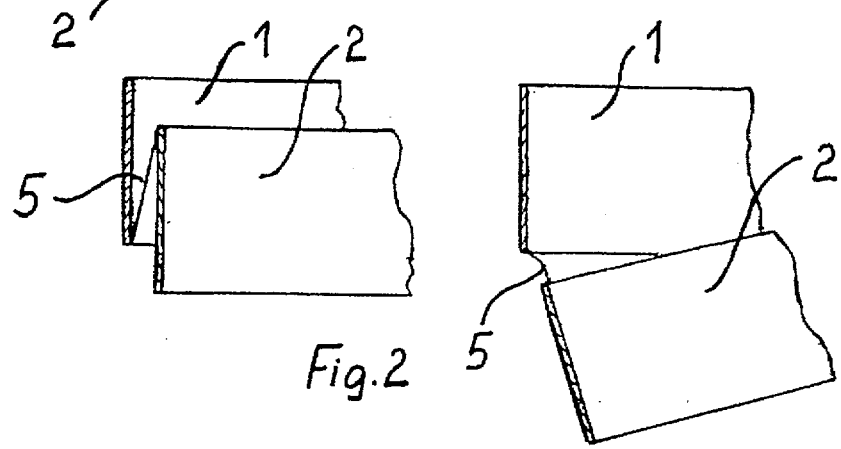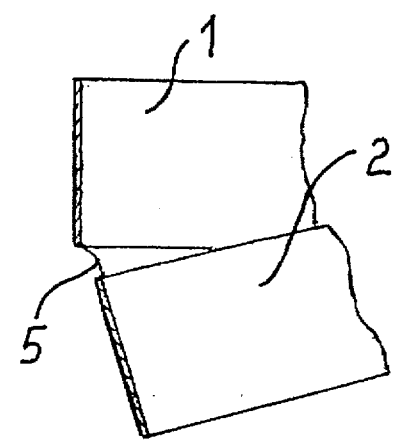
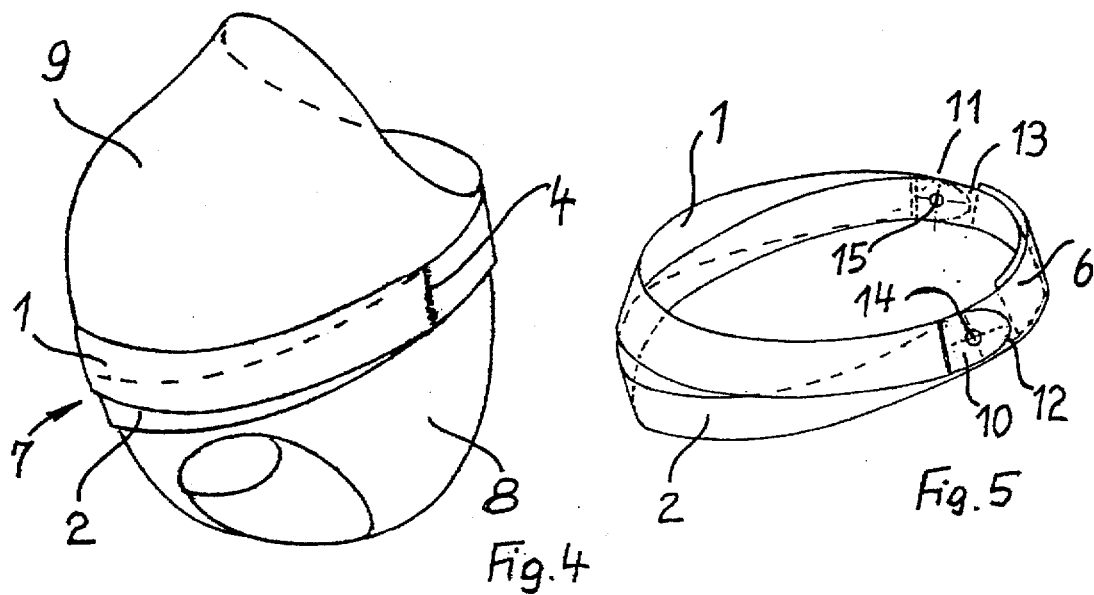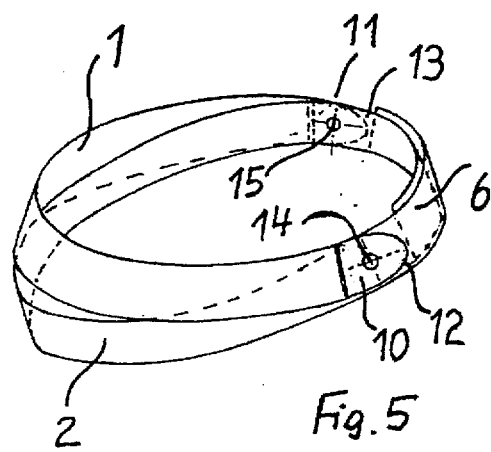

ABDOMINAL BELT

BACKGROUND OF THE INVENTION

The invention relates to an abdominal belt.

Abdominal belts as known from DE 87 08 327.2 U1 are designed as more or less wide strips made of a material which is elastic in the longitudinal direction of the belt, but is virtually nonelastic in the transverse direction of the belt. The known abdominal belts are not fully satisfactory in that this stiffness in the transverse direction results, in particular, in aggravating pressure being exerted on the groin area of the individuals wearing them when this individual is seated.

The object of the invention is to provide an abdominal belt which ensures large-surface-area support of the abdomen when the wearer is walking and standing without this large-surface-area support involving disadvantages when the wearer is seated. This object is achieved, in the case of the abdominal belt according to the invention, in that it has at least two merely longitudinally elastic supporting straps which overlap in an imbricated manner to a greater or lesser extent in the abdominal area, and in that the upper and lower borders of respectively successive supporting straps are connected to one another via in each case a longitudinally and transversely elastic fabric bridge.

SUMMARY OF THE INVENTION

The abdominal belt according to the invention provides the advantage that the supporting straps are pushed one over the other when the individual wearing them sits down, and the abdominal belt consequently narrows by an amount which rules out pressure being exerted locally, as would be the case with a single-part belt of the same effective width. The elastic supporting bridge connecting the respectively upper and lower borders of successive supporting straps to one another ensures, when the individual wearing the abdominal belt stands up, that the pushed-together supporting straps are moved back into their initial position again in the manner of an opening visor, in which position they support the lower abdomen over a large surface area and in which, consequently, the risk, known in the case of narrow abdominal belts, of their so-called "cutting into" the abdominal tissue is absent.

Further details and features of the invention can be gathered from the subclaims and from the following description of two embodiments illustrated in the accompanying drawing, in which:

FIG. 1 shows the perspective view of an abdominal belt,

FIG. 2 shows, schematically, the position of the supporting straps of the abdominal belt according to FIG. 1 when the wearer of the abdominal belt is seated, FIG. 3 shows, schematically, the position of the supporting straps of the abdominal belt according to FIG. 1 when the wearer of the abdominal belt is standing, FIG. 4 shows the use of an abdominal belt according to FIG. 1 in conjunction with a panty girdle, and FIG. 5 shows a modified embodiment of the abdominal belt according to FIGS. 1 to 3.

DESCRIPTION OF THE BEST MODES FOR CARRYING OUT THE INVENTION

The abdominal belt illustrated in FIGS. 1 to 3 has two supporting straps 1 and 2 which are connected directly to one another in the back area defined by transverse seams 3 and 4, while they are merely connected to one another indirectly, via a highly elastic fabric bridge 5, in the abdominal-belt front part which serves to support the lower abdomen. In other words, in the back area of the abdominal belt, the supporting straps 1 and 2 form two-layered sections of the abdominal belt. In order to be able to open and close the abdominal belt conveniently, the mutually interacting parts of a touch-and-close fastener 6 are connected to the abovementioned double-layered sections, said closure 6 also permitting the length of the belt to be changed. If the individual wearing the abdominal belt sits down, then the supporting straps 1 and 2 are pushed together in an imbricated manner, as is indicated in FIG. 2, to be precise with elastic expansion of the fabric bridge 5. In other words, the abdominal belt becomes narrower. As a result, the pressure exerted on the groin area by the abdominal belt remains negligible or at least within reasonable limits. When the wearer stands up again, the supporting straps 1 and 2 move back—not least due to the action of the elastic fabric bridge 5—into their initial position, indicated in FIG. 3. The abdominal belt is consequently adapted to the different requirements placed on it when the wearer is seated, standing or walking.

FIG. 4 shows the possibility of integrating an abdominal belt according to FIGS. 1 to 3 into a panty girdle for mothers-to-be. In this case, the abdominal belt 7 connects a panty part 8 to an abdominal part 9 which serves to provide additional support for the upper abdomen. Of course, it is also possible to combine an abdominal belt only with an abdominal part 9 or a panty part 8.

FIG. 5 illustrates a slightly modified embodiment of the abdominal belt according to FIGS. 1 to 3, in the case of which the ends of the supporting strap 1 are provided with tabs 10 and 11 which, in the same way as the sections 12 and 13 of the supporting strap 2 which are assigned to them, are reinforced by fabric, plastic or leather. In this case, the reinforced tabs 10 and 11 are connected to reinforced sections 12, 13 via hinges 14, 15. As a result, the modified abdominal belt is of only single-layer design in the back area.

I claim:

1. An abdominal belt having two elastic supporting straps extending substantially over the abdominal region of a user, and releasable connecting means in the region of the back of a user; said two supporting straps extending in a substantially longitudinal direction and being arranged to overlap in an imbricated manner substantially in the abdominal region of said user; and wherein upper and lower borders respectively, of two of said supporting straps (1, 2) successively oriented relative to each other, are connected to each other by a longitudinally and transversely extending elastic fabric bridge (5).

2. The abdominal belt as claimed in claim 1, wherein the ends of at least one of said supporting straps (1) are connected by longitudinal and transverse seams to longitudinally and transversely extending stiff sections of a touch-and-close fastener (6) comprising said releasable connecting means.

3. The abdominal belt as claimed in claim 2, wherein sections of the touch-and-close fastener (6) which extend over the entire height of the supporting straps (1,2), connected to one another in a congruent manner in the region of the back of the user, are of a width which permits the length of the abdominal belt to be changed.

4. The abdominal belt as claimed in claim 1, wherein the ends of one supporting strap (1) are provided with tabs (10,11) and are connected to the other supporting strap (2) via hinges (14,15).

5. The abdominal belt as claimed in claim 4, wherein, in the region in which said supporting straps are connected together, the supporting straps (1, 2) are provided with reinforcements made of fabric, plastic or leather.

6. The abdominal belt as claimed in claim 1, wherein the upper border of the uppermost supporting strap is adjoined by an elastic abdominal part (9) which serves for upper-abdomen support.

7. The abdominal belt as claimed in claim 1, wherein said abdominal belt comprises part of a panty girdle having an abdominal part (9) and a panty part (8).

* * * * *